United States Patent [19]

Friebe et al.

[11] Patent Number: 4,863,945

[45] Date of Patent: Sep. 5, 1989

[54] PYRROLOBENZIMIDAZOLES AND PHARMACEUTICAL COMPOSITIONS CONTAINING THEM

[75] Inventors: Walter-Gunar Friebe, Mannheim; Alfred Mertens, Schriesheim; Klaus Strein, Hemsbach; Erwin Boehm, Ladenburg, all of Fed. Rep. of Germany

[73] Assignee: Boehringer Mannheim GmbH, Mannheim, Fed. Rep. of Germany

[21] Appl. No.: 131,367

[22] Filed: Dec. 10, 1987

[30] Foreign Application Priority Data

Dec. 11, 1986 [DE] Fed. Rep. of Germany ....... 3642315

[51] Int. Cl.$^4$ .................. A61K 31/415; A61K 31/38; A61K 31/40; A61K 31/41; A61K 31/50; A61K 31/505; A61K 31/53; A61K 31/535; A61K 31/435; A61K 31/44; A61K 31/47; A61K 31/495; C07D 235/00; C07D 235/02; C07D 487/00; C07D 401/00

[52] U.S. Cl. .................. 514/393; 514/226.8; 514/227.2; 514/228.5; 514/228.8; 514/230.8; 514/232.8; 514/241; 514/242; 514/248; 514/249; 514/253; 514/254; 514/259; 514/260; 514/269; 514/272; 514/274; 514/307; 514/309; 514/310; 514/312; 514/313; 514/314; 514/322; 514/339; 514/361; 514/362; 514/363; 514/364; 514/365; 514/369; 514/370; 514/372; 514/374; 514/376; 514/377; 514/378; 514/380; 514/381; 514/383; 514/384; 544/310; 544/315; 544/316; 544/317; 544/318; 544/319; 544/320; 544/321; 544/322; 544/324; 544/326; 544/327; 544/328; 544/331; 544/333; 544/353; 544/354; 544/356; 544/366; 544/405; 544/60; 544/139; 544/179; 544/180; 544/182; 544/212; 544/237; 544/235; 544/238; 544/284; 544/298; 544/300; 546/139; 546/141; 546/142; 546/143; 546/144; 546/146; 546/147; 546/148; 546/152; 546/153; 546/155; 546/157; 546/159; 546/167; 546/171; 546/172; 546/174; 546/175; 546/176; 546/177; 546/178; 546/199; 546/271; 548/127; 548/128; 548/129; 548/134; 548/135; 548/136; 548/159; 548/182; 548/183; 548/184; 548/185; 548/186; 548/187; 548/189; 548/190; 548/191; 548/192; 548/193; 548/202; 548/194; 548/195; 548/198; 548/199

[58] Field of Search ........................ 548/326; 514/393; 548/203; 548/203; 548/204; 548/205; 548/207; 548/209; 548/210; 548/212; 548/213; 548/214; 548/217; 548/221; 548/222; 548/225; 548/226; 548/227; 548/228; 548/229; 548/230; 548/231; 548/232; 548/233; 548/235; 548/236; 548/241; 548/243; 548/244; 548/245; 548/246; 548/247; 548/250; 548/251; 548/252; 548/253; 548/254; 548/255; 548/262; 548/263; 548/264; 548/265; 548/267; 548/268; 548/269; 548/326

[56] References Cited

U.S. PATENT DOCUMENTS

4,666,923 5/1987 Hölck et al. .................. 514/338
4,695,567 9/1987 Mertens et al. ................ 514/253
4,710,510 12/1987 Mertens et al. ................ 514/394

FOREIGN PATENT DOCUMENTS

0214592 3/1987 European Pat. Off. ............ 548/326

*Primary Examiner*—Mary C. Lee
*Assistant Examiner*—J. Richter
*Attorney, Agent, or Firm*—Felfe & Lynch

[57] ABSTRACT

Pyrrolobenzimidazoles of the formula:

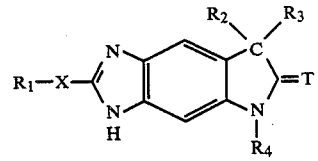

are useful for treatment of heart and circulatory diseases. $R_1$ is substituted phenyl; or optionally substituted naphthyl or a five- or six-membered heterocyclic group which can be condensed with a phenyl ring to form a bicyclic radical. $R_2$ is hydrogen, alkyl, alkenyl or cycloalkenyl; $R_3$ is alkyl, alkenyl or hydroxyalkyl or with $R_2$ together forms cycloakylene; or $R_2$ and $R_3$ together form alkylidene or cycloalkylidene. $R_4$ is hydrogen or lower alkanoyl. X is a valency bond, alkylene, vinylene, imino or carbonylamino. T stands for two hydrogen atoms. When X is a valency bond, $R_1$ can also be hydrogen, hydrocarbyl which may also contain oxygen, amino, sulfur, carbonyl and sulfonyl groups. When X is imino or carbonylamino or when $R_1$ is a bicyclic radical, T can also be oxygen. The compounds also include the tautomers and physiologically acceptable salts with inorganic and organic acids.

20 Claims, No Drawings

PYRROLOBENZIMIDAZOLES AND PHARMACEUTICAL COMPOSITIONS CONTAINING THEM

The present invention is concerned with new pyrrolobenzimidazoles, processes for the preparation thereof and pharmaceutical compositions containing them.

The new pyrrolobenzimidazoles according to the present invention are compounds of the general formula:

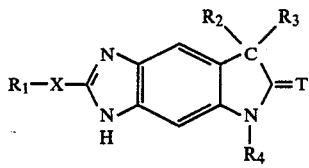

wherein $R_1$ is a phenyl ring of the general formula:

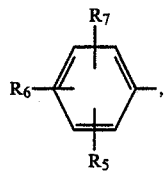

in which $R_5$, $R_6$ and $R_7$, which can be the same or different, each signifies a hydrogen atom or an alkanesulphonyloxy, trifluoromethanesulphonyloxy, alkanesulphonylamino, trifluoromethanesulphonylamino, N-alkylalkanesulphonylamino, N-alkyltrifluoromethanesulphonylamino, alkyl-sulphenylmethyl, alkylsulphinylmethyl or alkyl-sulphonylmethyl radical, a carbonyl group substituted by hydroxyl, alkoxy, amino, alkylamino or dialkylamino, a sulphonyl group substituted by amino, alkylamino, dialkylamino or cyclic imino in which a methylene group in the 4-position can be replaced by a sulphur or oxygen atom; an alkylcarbonylamino, aminocarbonylamino or alkylaminocarbonylamino radical, an alkylthio, alkylsulphinyl or alkylsulphonyl radical, nitro, halogen, amino, hydroxyl, alkyl, alkoxy, alkenyloxy, alkynyloxy, cyanoalkyloxy, carboxyalkyloxy, alkoxycarbonylalkyloxy, dialkylamino, 1-imidazolyl, trifluoromethyl or cyano or $R_1$ is a naphthyl radical or $R_1$ is a saturated or unsaturated heterocyclic five-membered ring with 1-4 heteroatoms or a saturated or unsaturated heterocyclic six-membered ring with 1-5 heteroatoms, the heteroatoms being the same or different and signifying oxygen, sulphur or nitrogen which, if desired, can carry an oxygen atom on one or more nitrogen atoms and the five- or six-membered rings are optionally substituted one or more times by alkyl, alkoxy, alkylthio, hydroxyl, nitro, amino, halogen or cyano or can be condensed with a phenyl ring to give a bicyclic radical or, when X represents a valency bond, $R_1$, besides the above-mentioned groups, can also signify a hydrogen atom or alkyl, cycloalkyl, alkenyl, cycloalkenyl, alkynyl, haloalkyl, alkoxyalkyl, carboxyalkyl, alkoxycarbonylalkyl, aminoalkyl, hydroxyalkyl, hydroxyl, mercapto, amino, alkylthio, alkylcarbonylamino, formylamino, alkylsulphonylamino, formylaminoalkyl, alkoxycarbonylaminoalkyl or alkylsulphonylaminoalkyl, $R_2$ is a hydrogen atom or an alkyl, alkenyl or a cycloalkyl radical; $R_3$ is an alkyl, alkenyl or hydroxyalkyl radical or, with $R_2$ together, represents a cycloalkylene radical; or $R_2$ and $R_3$ together form an alkylidene or cycloalkylidene radical, $R_4$ is a hydrogen atom or a lower alkanoyl radical, X is a valency bond or an alkylene, vinylene, imino (—NH—) or carbonylamino (—CONH—) radical, T stands for two hydrogen atoms, or, when X is an imino group (—NH—) or a carbonylamino group (—CONH—) or when $R_1$ is a heterocyclic five- or six-membered ring, which is condensed with a phenyl ring to give a bicyclic radical, T can also be an oxygen atom; the tautomers thereof and the physiologically acceptable salts thereof with inorganic and organic acids.

Since the compounds of general formula I, when $R_2$ is not the same as $R_3$, possess an asymmetric carbon atom, the optically-active forms and racemic mixtures of these compounds are also the subject of the present invention.

U.S. Pat. Nos. 4,666,923, 4,695,567 and 4,710,510 and Published European Patent Application No. 214 592 describe analogous compounds in which T exclusively signifies oxygen or sulphur. These compounds show a strongly inotropic action. The compounds of the present invention can also be used as medicaments for the treatment of heart and circulatory diseases. In particular, they influence the thrombocyte and erythrocyte aggregation and/or increase the heart power and/or have a vasodilatory action.

When $R_1$ is a phenyl ring of general formula II, then the alkyl moiety of the substituents mentioned in the case of $R_5$, $R_6$ and $R_7$ can contain 1 to 5 carbon atoms and preferably 1 to 4 carbon atoms. Preferred in this sense are, for example, the methanesulphonyloxy, ethanesulphonyloxy, n-propanesulphonyloxy, iso-propanesulphonyloxy, trifluoromethanesulphonyloxy, methylsulphenylmethyl, ethylsulphenylmethyl, n-propylsulphenylmethyl, methylsulphonylmethyl, ethylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino and propylaminocarbonylamino radicals; the methyl, ethyl, propyl, methoxy, ethoxy, propyloxy, allyloxy, but-2-enyloxy, but-3-enyloxy, pent-2-enyloxy, propargyloxy, but-2-ynyloxy, but-3-ynyloxy, cyanomethyloxy, cyanoethyloxy, methoxycarbonylmethyloxy, methoxycarbonylethyloxy, methylthio, ethylthio, methylsulphinyl, ethylsulphinyl, methylsulphonyl and ethylsulphonyl radicals.

In the case of sulphonyl groups which can be substituted by cyclic imino groups, the morpholino, pyrrolidino, piperidino and hexamethyleneiminosulphonyl radicals are preferred.

Especially preferably, $R_5$ is a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyltrifluoromethylsulphonylamino radical, a carbonyl group substituted by hydroxyl, alkoxy, amino, alkylamino or dialkylamino or a sulphonyl group substituted by amino, dialkylamino or morpholino, whereby each of the above-mentioned alkyl moieties can contain 1 or 2 carbon atoms, a nitro, cyano or alkylaminosulphonyl group with 1 to 4 carbon atoms, an alkylcarbonylamino, aminocarbonylamino or N-alkylaminocarbonylamino radical, an alkylthio, alkylsulphinyl or alkylsulphonyl radical, whereby each of the above-mentioned alkyl moieties can contain 1 or 2 carbon atoms, halogen, amino, hydroxyl, dialkylamino, alkyl, alkoxy, alkenyloxy or alkynyloxy, preferably with 1 to 3 carbon atoms, a cyanomethyloxy or methoxycarbonylmethyloxy radical, a trifluoromethyl radical or a 1-imidazolyl radical, $R_6$ a hydrogen atom, an alkyl radical with 1 to 3 carbon atoms, an alkoxy or dialkylamino radical with 1 or 2 carbon atoms in each alkyl moiety or a halogen atom and $R_7$ a hydrogen atom or a methoxy radical.

The phenyl part can carry 1 to 3 of the mentioned substituents.

Preferred monosubstituted phenyl compounds include the hydroxy-, $C_1$-$C_3$-alkyl-, $C_1$-$C_3$-alkoxy-, allyloxy-, propargyloxy-, cyanomethyloxy-, methoxycarbonylmethyloxy-, halo-, nitro-, cyano-, aminocarbonyl-, methoxycarbonyl-, amino-, $C_1$-$C_3$-dialkylamino-, $C_1$-$C_3$-alkylthio-, $C_1$-$C_3$-alkylsulphonyl-, $C_1$-$C_3$-alkylsulphonyloxy- and 1-imidazolyl-phenyls, the substituent being in the 2-, 3- or 4-position.

Preferred disubstituted phenyls contain, as substituents, an alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino, an alkylaminosulphonyl, alkylcarbonylamino, aminocarbonylamino or N-alkyl-aminocarbonylamino radical, a hydroxyl, alkyl, alkoxy, allyloxy, propargyloxy, cyanomethyloxy, methoxycarbonylmethyloxy, cyano, halogen, nitro, amino, dialkylamino, alkylthio, alkylsulphinyl, alkylsulphonyl or 1-imidazolyl radical, whereby the two substituents can be the same or different and can be in the 2,3-, 2,4-, 2,5-, 2,6-, 3,4- or 3,5-positions but preferably in the 2,4-, 2,5- or 3,4-positions and the above-mentioned alkyl radicals, alone or in combination with other radicals, can contain 1 to 3 carbon atoms.

The preferred trisubstituted phenyl radical is the 3,4,5-trimethoxyphenyl radical.

When $R_1$ is a heterocyclic five-membered ring with 1 to 4 heteroatoms or a heterocyclic six-membered ring with 1 to 5 heteroatoms, the heteroatoms of the above-mentioned five- and six-membered rings being the same or different and signifying nitrogen, oxygen or sulphur and possibly carrying an oxygen atom on one or more nitrogen atoms, then, in this case, there are preferred the pyrrole, furan, thiophene, pyrazole, imidazole, thiazole, isothiazole, oxazole, isoxazole, triazole, tetrazole, thiadiazole, oxadiazole, pyrazine, N,N'-dioxypyrazine, pyrimidine, N,N'-dioxypyrimidine, pyridazine, oxazine, thiazine, triazine, tetrazine, pyridine, N-oxypyridine, piperidine, piperazine, morpholine and thiomorpholine radicals.

Alkyl, alkoxy and alkylmercapto substituents in the heterocyclic five- and six-membered ring can contain 1 to 6 and preferably 1 to 4 carbon atoms, the methyl, ethyl, methoxy, ethoxy, methylthio and ethylthio radicals being preferred. Halogen is to be understood to mean fluorine, chlorine or bromine and preferably chlorine.

When the heterocyclic five- and six-membered rings are condensed with a phenyl ring, then the indole, indazole, benzimidazole, quinoline, isoquinoline, cinnoline, phthalazine, quinazoline, quinoxaline, benzofuran, benzothiophene, benzoxazole, benzisoxazole, benzothiazole and benzisothiazole radicals are preferred, as well as the naphthyl radical.

When X signifies a valency bond and $R_1$ an alkyl, alkenyl or alkynyl radical, then thereunder are to be understood straight or branched chains with up to 10 carbon atoms. Preferred in this sense are the methyl, ethyl, propyl, butyl, pentyl, hexyl, vinyl, propenyl and propynyl radicals. When X signifies a valency bond and $R_1$ a cycloalkyl or cycloalkenyl radical, then thereunder are to be understood rings with three to seven members. Preferred in this sense are the cyclopropyl, cyclobutyl, cyclopentyl, cyclohexyl, cyclopentenyl and cyclohexenyl radicals. When X signifies a valency bond and $R_1$ a haloalkyl, alkoxyalkyl, carboxyalkyl, alkoxycarbonylalkyl, hydroxyalkyl, aminoalkyl, alkoxycarbonylaminoalkyl, alkylsulphonylaminoalkyl, alkylthio or alkylcarbonylamino radical, then the alkyl or alkoxy moieties can contain 1 to 6 carbon atoms. Halogen is to be understood to be fluorine or chlorine and preferably fluorine.

Preferred in this sense are the trifluoromethyl, ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, aminomethyl, aminoethyl, aminopropyl, aminobutyl, hydroxymethyl, hydroxyethyl, hydroxypropyl, hydroxybutyl, methylthio, ethylthio, propylthio, butylthio, acetylamino, propionylamino, butyloxycarbonylamino, methylsulphonylamino, formylaminopropyl, acetylaminopropyl, propionylaminopropyl and methylsulphonylaminopropyl radicals.

When, in general formula I, $R_2$ and $R_3$ are alkyl radicals then thereunder are to be understood straight or branched alkyl chains with 1 to 6 carbon atoms. Preferred in this sense are the methyl, ethyl, propyl and butyl radicals.

When $R_2$ and $R_3$, together with the carbon atom to which they are attached, form a carbocyclic ring, then thereunder are to be understood rings with three to seven members, the cyclopropane, cyclobutane, cyclopentane and cyclohexane rings being preferred.

When, in general formula I, $R_4$ is an alkanoyl radical, then thereunder are to be understood straight-chained, branched and cyclic alkanoyl radicals with 1 to 7 carbon atoms. Preferred in this sense are the formyl, acetyl and propionyl radicals.

When, in general formula I, X is an alkylene radical, then thereunder are to be understood alkylene radicals with 1 to 4 carbon atoms, the methylene and ethylene radicals being preferred.

Especially preferred compounds of general formula I are those in which $R_1$ is a phenyl radical of general formula II, wherein $R_5$ is a hydrogen atom, a methanesulphonyloxy, trifluoromethanesulphonyloxy, methanesulphonylamino, trifluoromethanesulphonylamino, methylthio, methylsulphinyl, methylsulphonyl, hydroxyl, methyl, methoxy, propargyloxy, trifluoromethyl or 1-imidazolyl radical, $R_6$ is a hydrogen or chlorine atom or a methyl, methoxy or dimethylamino radical and $R_7$ is a hydrogen atom or a methoxy radical or $R_1$ is a pyrrole, furan, thiophene, pyrazole, imidazole, isothiazole, thiazole, oxazole, triazole, tetrazole, thiadiazole, isoxazole, oxadiazole, pyridine, N-oxypyridine, pyrazine, N,N'-dioxypyrazine, pyrimidine, N,N'-dioxypyrimidine, pyridazine, oxazine, thiazine, triazine, tetrazine, piperidine, piperazine, morpholine or thiomorpholine radical, as well as the methyl-, ethyl-, methoxy-, ethoxy-, methylthio-, ethylthio- and chlorine-substituted derivatives thereof or an indole, indazole, quinoline or isoquinoline radical or represents a naphthyl radical or $R_1$, when X represents a valency bond, besides the said groups, can also signify a hydrogen atom, a methyl, ethyl, propyl, butyl, pentyl, hexyl, propenyl, cyclopentyl, cyclohexyl, trifluoromethyl, hydroxyl, mercapto, methylthio, amino, acetamido or formamido radical, $R_2$ and $R_3$ are the same and signify methyl radicals or $R_2$ and $R_3$, together with the carbon atom to which they are attached, form a cyclopentane ring or cyclohexane ring, $R_4$ is a hydrogen atom or a formyl, acetyl, propionyl or butyryl radical and X is a valency bond, a methylene radical, an imino group or a carbonylamino group.

The process according to the present invention for the preparation of compounds of general formula I is characterised in that, in known manner, (a) a compound of the general formula:

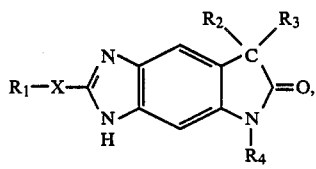

in which $R_1$, $R_2$, $R_3$, $R_4$ and X have the above-mentioned meanings, is reduced, or (b) a compound of the general formula:

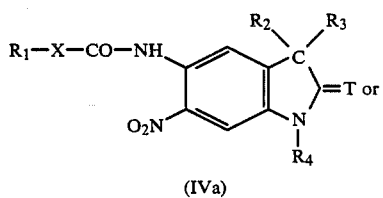

(IVa)

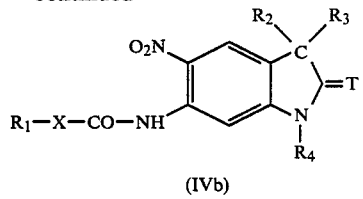

(IVb)

in which $R_1$, $R_2$, $R_3$, $R_4$, T and X have the above-mentioned meanings, is reduced and cyclised, or (c) a compound of the general formula:

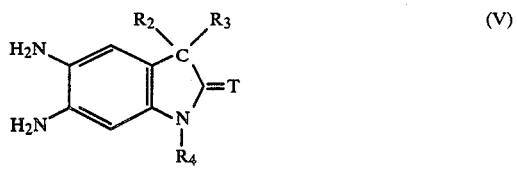

in which T, $R_2$, $R_3$ and $R_4$ have the above-mentioned meanings, is reacted with a compound of general formula:

in which X has the above-given meaning, Y is a hydrogen atom, a hydroxyl group or a group which is easily split off, W is an oxygen atom or, together with Y, represents a nitrogen atom and $R_1'$ has the meaning given above for $R_1$, with the exception that, when X represents a valency bond, $R_1'$ is not an amino, hydroxyl or mercapto group, or with a compound which transfers the carbonyl, thiocarbonyl or imino group, for example, phosgene, thiophosgene, 1,1'-carbonyldiimidazole, a chloroformic acid ester, a carbonic acid ester, urea or cyanogen bromide, and subsequently, if desired, a compound obtained of general formula I or a tautomer thereof is converted into another compound of general formula I and/or a compound obtained of general formula I is converted into a physiologically acceptable salt of an organic or inorganic acid.

The reduction mentioned in process (a) is preferably carried out in an aprotic solvent, for example, an ether, such as diethyl ether, dimethoxyethane, dioxan or tetrahydrofuran, with a complex metal hydride, for example, lithium aluminium hydride, at a temperature of from 0° to 100° C. and preferably at the boiling temperature of the solvent.

The reduction mentioned in process (b) is preferably carried out in a solvent or solvent mixture, such as water, methanol, ethanol, glacial acetic acid, ethyl acetate or dimethylformamide, with hydrogen in the presence of a catalyst, such as Raney nickel, platinum or palladium/charcoal; with a metal, such as iron, tin or zinc, in the presence of an acid; with a salt, such as ferrous sulphate, stannous chloride, sodium sulphide, sodium hydrogen sulphite or sodium dithionite; or with hydrazine in the presence of Raney nickel at a temperature of from 0° to 100° C. but preferably at ambient temperature. The cyclised compounds of general formula I are thereby mostly formed directly.

The cyclisation can, if desired, be completed in that, after the reduction, heating is carried out, preferably in a solvent or solvent mixture, such as ethanol, isopropanol, glacial acetic acid, benzene, toluene, chlorobenzene, glycol, ethylene glycol dimethyl ether, sulfolan or dimethylformamide, to a temperature of from 50° to 220° C. but preferably to the boiling temperature of the reaction mixture, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, sodium ethylate or potassium tert.-butylate. However, the cyclisation can also be carried out without the use of a solvent and/or condensation agent.

Amongst the compounds of general formula VI mentioned in process (c) are to be understood aldehydes, carboxylic acids, acid halides, such as acid chlorides, carboxylic acid esters, such as methyl and ethyl esters, carboxylic acid amides and other activated carboxylic acid derivatives, as well as anhydrides and nitriles.

When the compound of general formula VI is an aldehyde, then the reaction with compounds of general formula V takes place under oxidising conditions, preferably in alcoholic medium, with heating to reflux, in the presence of atmospheric oxygen and catalytic amounts of an acid, such as toluenesulphonic acid, or in the presence of atmospheric oxygen and of a catalyst, such as pyrolusite, in an acidic medium, for example in glacial acetic acid, at ambient temperature.

When the compound of general formula VI is a carboxylic acid or a nitrile, then the reaction with compounds of general formula V takes place in the presence of a water-removing agent, preferably in polyphosphoric acid, at a temperature of from 50° to 250° C. and preferably of from 100° to 200° C.

When the compound of general formula VI is a carboxylic acid derivative, then the reaction with compounds of general formula V takes place in an inert solvent, preferably in methylene chloride or pyridine. For completion of the cyclisation, heating is subsequently carried out in a solvent or solvent mixture, such as ethanol, isopropanol, glacial acetic acid, benzene, chlorobenzene, glycol, diethylene glycol dimethyl ether, sulfolan or dimethylformamide, to a temperature of from 50° to 250° C. but preferably to the boiling temperature of the solvent or solvent mixture used, optionally in the presence of a condensation agent, such as phosphorus oxychloride, thionyl chloride, p-toluenesulphonic acid, hydrochloric acid, sulphuric acid, phosphoric acid or polyphosphoric acid, or optionally also in the presence of a base, such as sodium hydroxide, potassium methylate or potassium tert.-butylate. However, the cyclisation can also be carried out without the use of a solvent and/or condensation agent.

The reactions described in process (c) with compounds which transfer a carbonyl, thiocarbonyl or imino group are preferably so carried out that phosgene is introduced into a hydrochloric acid solution of the compounds of general formula V or thiophosgene is added thereto and left to stand at ambient temperature or compounds of general formula V are heated with cyanogen bromide or urea without the use of a solvent or the compounds of general formula V are heated to the boil with 1,1'-carbonyldiimidazole in an inert solvent, such as dioxan.

The compounds of general formula III needed as starting material are known for co-assigned U.S. Pat. No. 4,666,923 issued on May 19, 1987, or can be obtained by analogous processes.

The compounds of general formulae IVa or IVb can be obtained, for example, by reacting compounds of the general formulae:

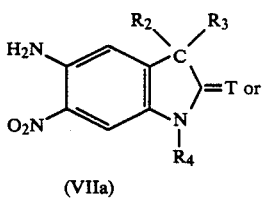

(VIIa)

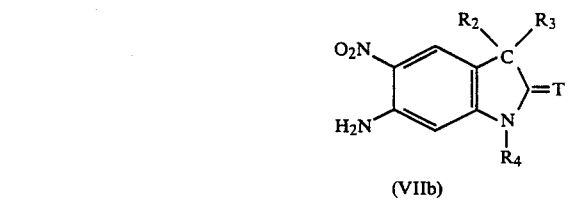

(VIIb)

in which T, $R_2$, $R_3$ and $R_4$ have the above-given meanings, with compounds of the general formula:

$R_1'—X—CO—Z$ (VIII), in which $R_1'$ and X have the above-given meanings and Z is a hydroxyl group or a residue which is easily split off.

The compounds of general formula V are obtained by the reduction of compounds of general formula VIIa or VIIb.

Compounds of general formula VIIa are obtained, for example, by nitration of 1-acyl-5-acylaminoindoline derivatives according to methods known from the literature and subsequent saponification of the 5-acyl radical.

Compounds of general formula VIIb are obtained, for example, by nitration of 1-acyl-6-acylaminoindoline derivatives according to methods known from the literature and subsequent saponification of the 6-acyl radical.

The conversion of compounds of general formula I into other compounds of general formula I applies, for example (a) for the reaction of a compound of general formula I, in which $R_1$ is an amino, aminoalkyl or cyclic imino group or is a heterocyclic five- or six-membered ring substituted with an amino group or is a phenyl ring of general formula II, in which one or more of the substituents $R_5$, $R_6$ and $R_7$ is an amino group and/or in which $R_4$ is a hydrogen atom, with carboxylic acids or with activated carboxylic acid derivatives, such as anhydrides or acid halides, to give formylamino or alkylcarbonylamino derivatives. The reactions are preferably carried out with carboxylic acid derivatives in the presence of a water-removing agent, for example polyphosphoric acid, or of a solvent forming an azeotropic mixture with water, such as benzene or toluene. Reactions with activated carboxylic acid derivatives are preferably carried out in an inert solvent, for example methylene chloride or pyridine, at a temperature of from 0° C. to 250° C. but preferably at the boiling temperature of the solvent.

(b) for reactions of compounds of general formula I, in which $R_1$ is an amino, aminoalkyl or cyclic imino group or $R_1$ is a heterocyclic five- or six-membered ring substituted with an amino group, such as is defined hereinbefore or $R_1$ is a phenyl ring of general formula II, in which one of the substituents $R_5$, $R_6$ and $R_7$ is an amino, N-alkylamino or hydroxyl group, with a sulphonic acid of the general formula:

$$R_8-SO_2OH \qquad (IX),$$

in which $R_8$ is an alkyl radical with 1 to 3 carbon atoms or a trifluoromethyl radical, or with a reactive derivative hereof, to give compounds of general formula I, in which the amino, aminoalkyl, cyclic imino, N-alkylamino or hydroxy radicals are sulphonated.

The reaction is preferably carried out in a solvent or solvent mixture, such as methylene chloride, diethyl ether, tetrahydrofuran, dioxan or benzene, optionally in the presence of an acid-binding agent, such as sodium carbonate, triethylamine or pyridine, whereby the latter two can simultaneously also be used as solvent, in the presence of an agent activating the acid or removing water, such as thionyl chloride or phosphorus pentachloride, but preferably with a reactive derivative of a compound of general formula IX, for example with an anhydride or halide thereof, such as methanesulphonic acid chloride or ethanesulphonic acid chloride, preferably at a temperature of from 0° to 100° C., for example at a temperature of from ambient temperature to 50° C.

(c) for the conversion of compounds of general formula I, in which $R_1$ is a phenyl ring of general formula II, whereby one of the substituents $R_5$, $R_6$ and $R_7$ is an alkylthio or alkylsulphenylmethyl radical with 1 to 3 carbon atoms in the alkyl moiety, to give compounds of general formula I, in which $R_1$ is a phenyl ring and one of the substituents $R_5$, $R_6$ and $R_7$ is alkylsulphinyl, alkylsulphonyl, alkylsulphinylmethyl or alkylsulphonylmethyl radical.

This oxidation is preferably carried out in a solvent or solvent mixture, for example in water, water/pyridine, acetone, glacial acetic acid, dilute sulphuric acid or trifluoroacetic acid, depending upon the oxidation agent used, preferably at a temperature of from −80° to 100° C.

For the preparation of an alkylsulphinyl or alkylsulphinylmethyl compound of general formula I, the oxidation is expediently carried out with one equivalent of the oxidation agent used, for example with hydrogen peroxide in glacial acetic acid, trifluoroacetic acid or formic acid at 0° to 20° C. or in acetone at 0° to 60° C.; with a per acid, such as performic acid, in glacial acetic acid or trifluoroacetic acid at 0° to 50° C. or with m-chloroperbenzoic acid in methylene chloride or chloroform at −20° C. to 60° C., with sodium metaperiodate in aqueous methanol or ethanol at −15° to 25° C., with bromine in glacial acetic acid or aqueous acetic acid, with N-bromosuccinimide in ethanol, with tert.-butyl hypochlorite in methanol at −80° C. to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride −70° C., the thioether-chlorine complex thereby obtained preferably being hydrolysed with aqueous ethanol.

For the preparation of an alkylsulphonyl or alkylsulphonylmethyl compound of general formula I, the oxidation is expediently carried out with one or with two or more equivalents of the oxidation agent used, for example hydrogen peroxide in glacial acetic acid, trifluoroacetic acid or in formic acid at 20° to 100° C. or in acetone at 0° to 60° C., with a per acid, such as performic acid, or m-chloroperbenzoic acid in glacial acetic acid, trifluoroacetic acid, methylene chloride or chloroform at a temperature of from 0° to 60° C., with nitric acid in glacial acetic acid at 0° to 20° C., with chromic acid or potassium permanganate in glacial acetic acid, water/sulphuric acid or in acetone at 0° to 20° C.

(d) for the conversion of compounds of general formula I, in which $R_1$ represents a phenyl ring of general formula II, whereby one of the substituents $R_5$, $R_6$ and $R_7$ is a carboxyl or hydroxysulphonyl group, to give compounds of general formula I, in which one of the substituents $R_5$, $R_6$ and $R_7$ is a carbonyl or sulphonyl group substituted by an amino, alkylamino or dialkylamino group. This takes place by reaction with an amine of the general formula $HNR_9R_{10}$, whereby $R_9$ and $R_{10}$ can be the same or different and signify hydrogen atoms or $C_1$–$C_5$-alkyl radicals, or with a reactive derivative hereof. It is advantageous to convert the carboxyl group or hydroxysulphonyl group into a reactive derivative, for example into an ester or an acid chloride, and then to react with the amine of the general formula $HNR_9R_{10}$.

The reaction is preferably carried out in a solvent or solvent mixture, such as methylene chloride, ethanol, chloroform, carbon tetrachloride, diethyl ether, tetrahydrofuran, dioxan, benzene, toluene, acetonitrile or dimethylformamide, optionally in the presence of an agent activating the acid or of a water-removing agent, for example in the presence of ethyl chloroformate, thionyl chloride, phosphorus trichloride, phosphorus pentoxide, N',N-dicyclohexylcarbodiimide/N-hydroxysuccinimide, N,N'-carbonyldiimidazole or N,N'-thionyldiimidazole or triphenylphosphine/carbon tetrachloride, or of an agent activating the amino group, for example phosphorus trichloride, and optionally in the presence of an inorganic base, such as sodium carbonate, or of a tertiary organic base, such as triethylamine or pyridine, which can simultaneously serve as solvent, at a temperature of from −25° to 250° C. but preferably at a temperature of from −10° C. and the boiling point of the solvent used. Furthermore, water formed during the reaction can be removed by azeotropic distillation, for example by heating with toluene on a water separator, or by adding a drying agent, such as anhydrous magnesium sulphate or a molecular sieve.

However, the reaction is carried out especially advantageously in a corresponding halide, for example a carboxylic acid or sulphonic acid chloride, and a corresponding amine, which can simultaneously serve as a solvent, and at a temperature of from 0° to 50° C.

(e) for the conversion of compounds of general formula I, in which $R_1$ is a phenyl ring of general formula II and one of the substituents $R_5$, $R_6$ or $R_7$ is a cyano group and/or in which $R_4$ is an alkanoyl radical, to give compounds of general formula I, in which $R_1$ is a phenyl ring of general formula II and one of the substituents $R_5$, $R_6$ or $R_7$ is an alkoxycarbonyl or aminocarbonyl radical or a carboxyl group and/or in which $R_4$ is a hydrogen atom.

This alcoholysis and/or hydrolysis is carried out either in the presence of an acid, such as hydrochloric acid, sulphuric acid, phosphoric acid or trichloroacetic acid, or in the presence of a base, such as sodium hydroxide or potassium hydroxide, in an appropriate solvent, such as water, water/methanol, ethanol, water/e- thanol, water/isopropanol or water/dioxan, at a temperature of from $-10°$ to $120°$ C., for example at a temperature from ambient temperature to the boiling temperature of the reaction mixture.

(f) for the alkylation of compounds of general formula I, in which $R_1$ is a phenyl ring of general formula II in which one of the substituents $R_5$, $R_6$ or $R_7$ is a hydroxyl or mercapto group or in which $R_1$ is a heterocyclic ring substituted with a hydroxyl or mercapto group or in which X is a valency bond and $R_1$ is a hydroxyl or mercapto group. The corresponding alkylmercapto or alkyloxy compounds are thereby obtained.

The reactions are preferably carried out in a solvent, such as acetone, ether, benzene, toluene or dimethylformamide, at a temperature of from $-30°$ C. to $+100°$ C. and preferably at ambient temperature, in the presence of a base, such as potassium carbonate or sodium hydride, and of an alkylation agent, such as an alkyl halide or alkyl sulphate.

(g) for the reduction of compounds of general formula I, in which $R_1$ represents a pyridine ring, to give compounds of general formula I, in which $R_1$ is a piperidine ring. The reduction is preferably carried out in an alcoholic medium in the presence of a catalyst, such as platinum or palladium, by means of hydrogen at normal pressure or at a slightly increased pressure and at a temperature between ambient temperature and $60°$ C.

(h) for the hydrogenation of a vinyl compound (X= —CH=CH—) to give the corresponding ethyl compound (X=—CH$_2$—CH$_2$). The hydrogenation is preferably carried out in a solvent, such as water, water/ethanol, methanol, glacial acetic acid, ethyl acetate or dimethylformamide, preferably with hydrogen in the presence of a hydrogenation catalyst, such as Raney nickel, platinum or palladium/charcoal.

(i) for the oxidation of a five- or six-membered ring with one or more nitrogen atoms to give the corresponding N-oxides. The oxidation is preferably carried out with one or more equivalents of the oxidation agent used, for example with hydrogen peroxide in glacial acetic acid, trifluoroacetic acid or in formic acid at $20°$ to $100°$ C. or in acetone at $0°$ to $60°$ C., with a per acid, such as performic acid or m-chloroperbenzoic acid, in glacial acetic acid, trifluoroacetic acid, methylene chloride or chloroform at a temperature of from $0°$ to $60°$ C.

Furthermore, the compounds obtained of general formula I can subsequently, if desired, be converted into their physiologically acceptable acid-addition salts with inorganic or organic acids. As acids herefor, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

For the preparation of pharmaceutical compositions, the compounds of general formula I are mixed in known manner with appropriate pharmaceutical carrier substances, aroma, flavouring and colouring materials and formed, for example, into tablets or dragees or, with the addition of appropriate adjuvant materials, suspended or dissolved in water or an oil, for example olive oil.

The new compounds according to the present invention of general formula I and the salts thereof can be administered enterally or parenterally in liquid or solid form. As injection medium, water is preferably used which contains the additives usual in the case of injection solutions, such as stabilising agents, solubilising agents or buffers.

Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Sold carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The compounds according to the present invention are usually administered in amounts of from 10 to 500 mg. per day, referred to 75 kg. body weight. It is preferred to administer 2 to 3 times per day 1 or 2 tablets with an active material content of 5 to 200 mg. The tablets can also be retarded in which case it is only necessary to give 1 or 2 tablets with 10 to 500 mg. of active material once per day. The active material can also be given by injection 1 to 8 times per day or by continuous infusion, amounts of 5 to 200 mg./day thereby normally being sufficient.

Preferred compounds according to the present invention are, apart from those mentioned in the Examples, also the following and the tautomers thereof:

7,7-dimethyl-2-(4-methylphenyl)-6,7-dihydro-3H,5H-pyrrolo[2,3-f]benzimidazole 7,7-dimethyl-2-(2-methoxy-4-methylphenyl)-6,7-dihydro-3H,5H-pyrrolo[2,3-f]benzimidazole 7,7-dimethyl-2-(4-trifluoromethylphenyl)-6,7-dihydro-3H,5H-pyrrolo[2,3-f]benzimidazole 7,7-dimethyl-2-(2-methoxy-4-trifluoromethylphenyl)-6,7-dihydro-3H,5H-pyrrolo[2,3-f]benzimidazole 7,7-dimethyl-2-(4-methylthiophenyl)-6,7-dihydro-3H,5H-pyrrolo[2,3-f]benzimidazole 7,7-dimethyl-2-(2-methoxy-4-methylthiophenyl)-6,7-dihydro-3H,5H-pyrrolo[2,3-f]benzimidazole 7,7-dimethyl-2-(4-methylsulphinylphenyl)-6,7-dihydro-3H,5H-pyrrolo[2,3-f]benzimidazole 7,7-dimethyl-2-(2-methoxy-4-methylsulphinylphenyl)-6,7-dihydro-3H,5H-pyrrolo[2,3-f]benzimidazole 7,7-dimethyl-2-(4-methylsulphonylphenyl)-6,7-dihydro-3H,5H-pyrrolo[2,3-f]benzimidazole 7,7-dimethyl-2-(4-methylsulphonyloxyphenyl)-6,7-dihydro-3H,5H-pyrrolo[2,3-f]benzimidazole 7,7-dimethyl-2-(2-methoxy-4-methylsulphonyloxyphenyl)-6,7-dihydro-3H,5H-pyrrolo[2,3-f]benzimidazole 7,7-dimethyl-2-(4-naphthyl)-6,7-dihydro-3H,5H-pyrrolo[2,3-f]benzimidazole 7,7-dimethyl-2-(2-methoxyphenyl)-6,7-dihydro-3H,5H-pyrrolo[2,3-f]benzimidazole 7,7-dimethyl-2-(1-imidazolyl)-6,7-dihydro-3H,5H-pyrrolo[2,3-f]benzimidazole 7,7-dimethyl-2-(4-thiomorpholinyl)-6,7-dihydro-3H,5H-pyrrolo[2,3-f]benzimidazole.

The following Examples are given for the purpose of illustrating the present invention:

EXAMPLE 1

2,7,7-Trimethyl-6,7-dihydro-3H,5H-pyrrolo[2,3-f]benzimidazole dihydrochloride (a) A mixture of 60.4 g. (0.41 mole) 3,3-dimethylindoline (Can. J. Chem. 29, 44/1951) and 90 ml. acetic anhydride is heated to reflux for 30 minutes. The reaction mixture is then poured on to ice and filtered to give 74.0 g. (95% of theory) N-acetyl-3,3-dimethylindoline; m.p. 99°–101° C.

(b) To 130 ml. concentrated sulphuric acid are added at 5° C. 62.4 g. (0.33 mole) N-acetyl-3,3-dimethylindoline. A mixture of 14.6 ml. 100% nitric acid and B 14.6 ml. concentrated sulphuric acid is added dropwise thereto, with cooling, stirred for 1 hour in an ice bath, poured on to ice, filtered and recrystallised from 2-propanol. There are obtained 68.8 g. (89% of theory) N-acetyl-3,3-dimethyl-5-nitroindoline; m.p. 172°–174° C.

(c) A solution of 50.0 g. (0.21 mole) N-acetyl-3,3-dimethyl-5-nitroindoline in 500 ml. methanol and 500 ml. tetrahydrofuran is hydrogenated over 5 ml. Raney nickel at 40° C. and 1 bar hydrogen pressure. After filtration, concentration and trituration with diethyl ether, there are obtained 36.3 g. (83% of theory) N-acetyl-5-amino-3,3-dimethylindoline; m.p. 117°–119° C.

(d) A mixture of 44.0 g. (0.22 mole) N-acetyl-5-amino-3,3-dimethylindoline and 60 ml. acetic anhydride is heated to reflux for 30 minutes, cooled, poured on to ice and filtered. The filter residue is taken up in methanol, mixed with sodium bicarbonate solution until a basic reaction is obtained, filtered, dried and evaporated to give 48 g. (91% of theory) 5-acetamido-1-acetyl-3,3-dimethylindoline; m.p. 190°–191° C.

(e) To 60 ml. acetic anhydride are added 24.6 g. (0.1 mole) 5-acetamido-1-acetyl-3,3-dimethylindoline and 5.0 ml. 100% nitric acid added dropwise thereto, while cooling. After stirring for 30 minutes at 25°–30° C., the reaction mixture is poured on to ice and filtered. There are obtained 25.8 g. (79% of theory) 5-acetamido-1-acetyl-3,3-dimethyl-6-nitroindoline; m.p. 222°–224° C.

(f) 4.3 g. 5-acetamido-1-acetyl-3,3-dimethyl-6-nitroindoline are hydrogenated analogously to Example 1(c) to give 3.9 g. (100% of theory) 5-acetamido-1-acetyl-6-amino-3,3-dimethylindoline; m.p. 88°–90° C.

(g) 3.9 g. 5-Acetamido-1-acetyl-6-amino-3,3-dimethylindoline are heated for 3 hours to reflux with 100 ml. saturated ethanolic hydrogen chloride solution, then evaporated and the residue recrystallized from isopropanol to give 3.4 g. (83% of theory) of the title compound; m.p. 255°–260° C. (decomp.).

EXAMPLE 2

7,7-Dimethyl-1,2,6,7-tetrahydro-3H,5H-pyrrolo[2,3-f]benzimidazol-2-one hydrochloride (a) A mixture of 37.5 g. (0.13 mole) 5-acetamido-1-acetyl-3,3-dimethyl-6-nitroindoline (Example 1(e), 250 ml. ethanol and 500 ml. 2N aqueous sodium hydroxide solution is stirred for 6 hours at 50° C. After filtering off, there remain 29.6 g. (92% of theory) 1-acetyl-5-amino-3,3-dimethyl-6-nitroindoline; m.p. 220°–221° C.

(b) 15.0 g. (0.06 mole) 1-Acetyl-5-amino-3,3-dimethyl-6-nitroindoline are hydrogenated in 300 ml. ethanol and 100 ml. tetrahydrofuran over 2 g. Raney nickel at 30° C. and 1 bar hydrogen pressure. After filtration and evaporation, there remain 12 g. (91% of theory) 1-acetyl-5,6-diamino-3,3-dimethylindoline in the form of an oil from which, with excess ethereal hydrogen chloride solution, there is obtained the dihydrochloride; m.p. 238°–240° C.

(c) 6.0 g. (0.02 mole) 1-Acetyl-5,6-diamino-3,3-dimethylindoline dihydrochloride are dissolved in 50 ml. 2N hydrochloric acid. Phosgene is passed through this solution for 2 hours and subsequently flushed with nitrogen, left to stand overnight, filtered off and the precipitate washed with water. There are obtained 4.7 g. (96% of theory) 5-acetyl-7,7-dimethyl-1,2,6,7-tetrahydro-3H,5H-pyrrolo[2,3-f]benzimidazol-2-one; m.p. above 300° C.

(d) 3.0 g. (13 mmole) 5-Acetyl-7,7-dimethyl-1,2,6,7-tetrahydro-3H,5H-pyrrolo[2,3-f]benzimidazol-2-one are heated under reflx for 3 hours in 100 ml. saturated ethanolic hydrogen chloride solution, then evaporated and the residue recrystallised from ethanol to give 2.3 g. (74% of theory) of the title compound; m.p. above 300° C.

EXAMPLE 3

7,7-Dimethyl-6,7-dihydro-2-phenyl-3H,5H-pyrrolo[2,3-f]benzimidazole dihyrochloride (a) To a solution of 5.0 g. (0.02mole) 1-acetyl-5-amino-3,3-dimethyl-6-nitroindoline (Example 2a) in 130 ml. tetrahydrofuran and 7.0 ml. triethylamine are added dropwise 3.5 g. (0.025 mole) benzoyl chloride in 20 ml. tetrahydrofuran. The reaction mixture is heated to reflux for 6 hours, evaporated, mixed with water, extracted with dichloromethane, the extract evaporated and the residue triturated with diethyl ether to give 6.4 g. (91% of theory) 1-acetyl-5-benzamido-3,3-dimethyl-6-nitroindoline; m.p. 186°–187° C.

(b) By hydrogenation of the above compound analogously to Example 2(b), there is obtaned a quantitative yield of 1-acetyl-6-amino-5-benzamido-3,3-dimethylindoline; m.p. 208°–210° C.

(c) By treatment with ethanolic hydrogen chloride solution analogously to Example 1 (g), from the above compound there is obtained, in 97% yield, the title compound; m.p. 273°–275° C.

EXAMPLE 4

5-Acetyl-7,7-dimethyl-6,7-dihydro-3H,5H-pyrrolo[2,3-f]benzimidazole

A mixture of 3.0 g. (0.01 mole) 1-acetyl-5,6-diamino-3,3-dimethylindoline dihydrochloride (Example 2b) and 35 ml. formamide is heated to reflx for 40 minutes and then evaporated. The residue is mixed with water, extracted with dichloromethane and the extract evaporated to give 2.6 g. (85% of theory) of the title compound; m.p. 214°–216° C.

EXAMPLE 5

7,7-Dimethyl-6,7-dihydro-3H,5H-pyrrolo[2,3-f]benzimidazole dihydrochloride

By treatment with ethanolic hydrogen chloride solution analogously to Example 1(g,) from the compound of Example 4 there is obtained, in 66% yield, the title compound; m.p. 248°–250° C.

EXAMPLE 6

5-Acetyl-7,7-dimethyl-6,7-dihydro-2-trifluoromethyl-3H,5H-pyrrolo[2,3-f]benzimidazole A mixture of 60 g. polyphosphoric acid, 1.6 ml. trifluoroacetic acid, 18 g. phosphorus pentoxide and 4.0 g. (18 mmole) 1-acetyl-5,6-diamino-3,3-dimethylindoline (Example 2b) is stirred for 7 hours at 150°–160° C. The reaction mixture is allowed to cool to 90° C., poured on to ice, left to stand overnight and filtered to give 1.7 g. (31%) of the title compound; m.p. 290°–291° C.

EXAMPLE 7

7,7-Dimethyl-6,7-dihydro-2-trifluoromethyl-3H,5H-pyrrolo[2,3-f]benzimidazole dihydrochloride 1.7 g. (5.7 mmole) of the compound of Example 6 is heated under reflux for 6 hours with 40 ml. 50% trifluoroacetic acid, then poured on to ice, washed with dichloromethane and the extract evaporated. The residue is taken up in acetone, mixed with excess ethereal hydrogen chloride solution and filtered to give 1.1 g. (59% of theory) of the title compound; m.p. 189°–192° C.

EXAMPLE 8

7,7-Dimethyl-6,7-dihydro-2-ethyl-3H,5H-pyrrolo[2,3-f]benzimidazole dihydrochloride (a) A mixture of 7.2 g. (28 mmole) 1-acetyl-5-amino-3,3-dimethyl-6-nitroindoline (Example 2a) and 7 ml. propionic acid anhydride is heated to 120° C. for 30 minutes, then poured on to ice and filtered to give 8.1 g. (95% of theory) 1-acetyl-3,3-dimethyl-6-nitro-5-propionamidoindoline; m.p. 178°–180° C.

(b) 7.5 g. (25 mmole) of the above compound are hydrogenated analogously to Example 1(c) to give 6.1 g. (89% of theory) 1-acetyl-6-amino-3,3-dimethyl-5-propionamidoindoline; m.p. 215°–219° C.

(c) 3.0 g. (11 mmole) of the above compound are treated analogously to Example 1(g). with ethanolic hydrogen chloride solution to give 2.7 g. (86% of theory) of the title compound; m.p. 256°–258° C.

EXAMPLE 9

7,7-Dimethyl-6,7-dihydro-2-(pyridin-3-yl)-3H,5H-pyrrolo[2,3-f]benzimidazole (a) A mixture of 3.6 g. (15 mmole) 1-acetyl-5-amino-3,3-dimethyl-6-nitroindoline (Example 2a), 150 ml. dichloromethane, 5.1 g. sodium bicarbonate and 5.1 g. nicotinoyl chloride hydrochloride is heated to reflux for 6 hours, then mixed with water, extracted with dichloromethane and the extract evaporated. After trituration with ether, there are obtained 3.7 g. (70% of theory) 1-acetyl-3,3-dimethyl-5-nicotinoylamino-6-nitroindoline; m.p. 251°–252° C.

(b) By hydrogenation of the above compound analogously to Example 1c, there is obtained, with 96% yield, 1-acetyl-6-amino-3,3-dimethyl-5-nicotinoylaminoindoline in the form of an oil.

(c) 2.0 g. of the above compound are stirred for 3 hours at 90° C. in 40 ml. concentrated hydrochloric acid, allowed to cool, rendered ammoniacal and filtered to give 0.8 g. (52% of theory) of the title compound; m.p. 213°–215° C.

EXAMPLE 10

5-Acetyl-7,7-dimethyl-6,7-dihydro-2-(pyridazin-4-yl)-3H,5H-pyrrolo[2,3-f]benzimidazole To 75 g. polyphoshoric acid are added 3.1 g. pyridazine-4-carboxylic acid, 5.0 g. (23 mmole) 1-acetyl-5,6-diamino-3,3-dimethylindoline (Example 2b) and 22 g. phosphorus pentoxide and heated to 150°–160° C. for 7 hours. The reaction mixture is poured on to ice, rendered ammoniacal, extracted with dichloromethane and the extract evaporated to give 3.6 g. (51% of theory) of the title compound in the form of a dark solid; m.p. 225°–260° C.

EXAMPLE 11

7,7-Dimethyl-6,7-dihydro-2-(pyridazin-4-yl)-3H,5H-pyrrolo[2,3-f]benzimidazole dihydrochloride By treatment with ethanolic hydrogen chloride solution analogously to Example 1g, from the compound of Example 10 there is obtained, in 45% yield, the title compound; m.p. 234°–236° C.

EXAMPLE 12

7,7-Dimethyl-6,7-dihydro-2-(pyridin-4-yl)-3H,5H-pyrrolo[2,3-f]benzimidazole

To a suspension of 3.5 g. lithium aluminium hydride in 100 ml. tetrahydrofuran is added dropwise at ambient temperature a solution of 5.3 g. (19 mmole) 7,7-dimethyl-6,7-dihydro-2-(pyridin-4-yl)-3H,5H-pyrrolo[2,3-f]benzimidazol-6-one. The reaction mixture is heated to reflux for 6 hours, decomposed with an aqueous solution of sodium chloride, extracted with dichloromethane and methanol, dried, evaporated and chromatographed on silica gel, 1.9 g. (38% of theory) of the title compound being eluted; m.p. 147°–149° C.

EXAMPLE 13

In a manner analogous to that described in Example 12, there are obtained the following compounds:

| designation | yield % | m.p. °C. (solvent) |
|---|---|---|
| (a) 7,7-dimethyl-2-(3-methyl-pyrazol-5-yl)-6,7-dihydro-3H,5H—pyrrolo[2,3-f]benzimidazole from the corresponding 6-oxo-derivative | 76 | 243–247 (methanol) |
| (b) 7,7-dimethyl-2-(4-quinolinyl)-6,7-dihydro-3H,5H—pyrrolo[2,3-f]benzimidazole from the corresponding 6-oxo-derivative (Example 14 b) | 50 | 287–291 (ethanol) |

EXAMPLE 14

In a manner analogous to that described in Example 10, there are obtained the following compounds:

| designation | Yield % | m.p. °C. (solvent) |
|---|---|---|
| (a) 2-(3-quinolinyl)-7,7-dimethyl-6,7-dihydro-3H,5H—pyrrolo[2,3-f]benzimidazol-6-one from 5,6-diamino-3,3-dimethylindolin-2-one and quinoline-3-carboxylic acid | 78 | over 300 (methanol) |
| (b) 2-(4-quinolinyl)-7,7-dimethyl-6,7-dihydro-3H,5H—pyrrolo[2,3-f]benzimidazol-6-one from 5,6-diamino-3,3-dimethylindolin-2-one and quinoline-4-carboxylic acid | 67 | 210–213 (ethanol) |
| (c) 7,7-dimethyl-2-(2-indolyl)-6,7-dihydro-3H,5H—pyrrolo-[2,3-f]benzimidazol-6-one from 5,6-diamino-3,3-dimethyl-indolin-2-one and indole-2-carboxylic acid | 29 | over 350 (ethanol) |
| (d) 7,7-dimethyl-2-(3-pyridyl-amino)-6,7-dihydro-3H,5H—pyrrolo[2,3-f]benzimidazol-6-one from 5,6-diamino-3,3-dimethylindolin-2-one and 3-cyanoaminopyridine | 22 | 206–208 (methanol) |

-continued

| designation | Yield % | m.p. °C. (solvent) |
|---|---|---|
| (e) 2'-(4-quinolinyl)spirocyclopentane-1,7'-6',7'-dihydro-3'H,5'H—pyrrolo-[2',3'-f]-benzimidazol)-6'-one from 5',6'-diamino-spiro(cyclopentan-1,3'-indolin)-2'-one and quinoline-4-carboxylic acid | 16 | 232–234 (ethyl acetate) |
| (f) 5-acetyl-7,7-dimethyl-6,7-dihydro-2-(imidazol-1-yl-methyl)-3H,5H—pyrrolo[2,3-f]benzimidazol from 1-acetyl-5,6-diamino-3,3-dimethyl-indoline and imidazole-1-acetic acid | 24 | above 280 (dichloromethane) |
| (g) 7,7-dimethyl-6,7-dihydro-2-(indol-3-yl-methyl)-3H,5H—pyrrolo[2,3-f]benzimidazol-6-one from 5,6-diamino-3,3-dimethyl-indolin-2-one and indole-3-acetic acid | | |
| (h) 2'-(2-indolyl)spiro(cyclopentane-1,7'-6',7'-dihydro-3'H,5'H—pyrrolo[2',3'-f]-benzimidazol)-6'-one from 5',6'-diamino-spiro(cyclopentane-1',3'-indolin)-2'-one and indol-2-carboxylic acid | | |
| (i) 2'-(4-indolyl)spiro(cyclopentane-1,7'-6',7'-dihydro-3'H,5'H—pyrrolo[2',3'-f]-benzimidazol)-6'-one from 5',6'-diamino-spiro(cyclopentane-1',3'-indolin)-2'-one and indol-4-carboxylic acid | | |
| (j) 2'-(5-indolyl)spiro(cyclopentane-1,7'-6',7'-dihydro-3'H,5'H—pyrrolo[2',3'-f]-benzimidazol)-6'-one from 5',6'-diamino-spiro(cyclopentane-1',3'-indolin)-2'-one and indol-5-carboxylic acid | | |
| (k) 2'-(6-indolyl)spiro(cyclopentane-1,7'-6',7'-dihydro-3'H,5'H—pyrrolo[2',3'-f]-benzimidazol)-6'-one from 5',6'-diamino-spiro(cyclopentane-1',3'-indolin)-2'-one and indol-6-carboxylic acid | | |

EXAMPLE 15

7,7-Dimethyl-6,7-dihydro-2-(4-methoxybenzoylamino)-3H,5H-pyrrolo[2,3-f]benzimidazol-6-one (a) 20 g. (104.6 mmole) 5,6-Diamino-3,3-dimethylindolin-2-one are suspended in 300 ml. ethanol, mixed with 12.2 g. cyanogen bromide and stirred for 2.5 hours at 25° C. The evaporation residue is again dissolved in ethanol, the ethanol is substantially distilled off and the residue is mixed with acetone and crystallised. There are obtained 25.7 g. (82% of theory) 2-amino-7,7-dimethyl-6,7-dihydro-3H,5H-pyrrolo[2,3-f]benzimidazol-6-one hydrobromide; m.p. 300°–305° C.

(b) 3 g. (10.1 mmole) 2-Amino-7,7-dimethyl-6,7-dihydro-3H,5H-pyrrolo[2,3-f]benzimidazol-6-one hydrobromide are stirred with 2.5 g. p-anisoyl chloride in 50 ml. pyridine for 4 hours at 50° C. The pyridine is subsequently distilled off, the residue is worked up with water, decanted, worked up with ligroin and the residue recrystallised twice from ethanol to give 1.4 g. (40% of theory) of the title compound; m.p. >300° C.

EXAMPLE 16

The following compounds were obtained in a manner analogous to that described in Example 15:

| designation | yield % | m.p. °C. (solvent) |
|---|---|---|
| (a) 7,7-dimethyl-6,7-dihydro-2-(benzoylamino)-3H,5H—pyrrolo-[2,3-f]benzimidazol-6-one | 34 | 315 (ethanol) |
| (b) 7,7-dimethyl-6,7-dihydro-2-(2-methoxybenzoylamino)-3H,5H—pyrrolo[2,3-f]benzimidazol-2-one | 57 | 277–278 (ethanol) |
| (c) 7,7-dimethyl-6,7-dihydro-2-(4-methylbenzoylamino)-3H,5H—pyrrolo[2,3-f]benzimidazol-6-one | 49 | >300 (ethanol) |
| (d) 7,7-dimethyl-6,7-dihydro-2-(4-trifluoromethylbenzoyl-amino)-3H,5H—pyrrolo[2,3-f]-benzimidazol-6-one | 57 | >300 (ethanol) |
| (e) 2'-benzoylamino-spiro(cyclopentan-1,7'-6',7'-dihydro-3'H,5'H—pyrrolo[2',3'-f]-benzimidazol)-6'-one | 75 | >300 (methanol) |
| (f) 2'-(4-methoxybenzoylamino)-spiro(cyclopentan-1,7'-6',7'-dihydro-3'H,5'H—pyrrolo-[2',3'-f]benzimidazol)-6'-one | 62 | >300 (methanol) |
| (g) 5-acetyl-7,7-dimethyl-6,7-dihydro-2-(4-pyridylcarbonyl-amino)-3H,5H—pyrrolo[2,3-f]-benzimidazole from 5-acetyl-2-amino-7,7-dimethyl-6,7-dihydro-3H,5H—pyrrolo[2,3-f]-benzimidazole | 55 | above 280 (water) |
| (h) 2'-(4-pyridinecarbonylamino)-spiro(cyclopentane-1,7'-6',7'-dihydro-3'H,5'H—pyrrolo-[2',3'-f]benzimidazol)-6'-one | 56 | >300 (methanol) |

EXAMPLE 17

6,7-Dihydro-7,7-dimethyl-2-(4-methoxyphenylamino)-3H,5H-pyrrolo[2,3-f]benzimidazol-6-one 3 ml. 4-Methoxyphenyl isothiocyanate are added dropwise to a solution of 3.8 g. 5,6-diamino-3,3-dimethylindolin-2-one in 20 ml. dry ethanol. The reaction mixture is stirred for 3 hours at 60° C., the solvent is removed in a vacuum, the residue is suspended in water and extracted with dichloromethane. The organic phase is dried over anhydrous sodium sulphate, filtered and the solvent removed in a vacuum to give 7.5 g. of residue, 6.8 g. of which are dissolved in 1 liter dichloromethane. 8 ml. Triethylamine and 16 g. mercurous chloride are added thereto and the reaction mixture boiled under reflux for 3 days. The solvent is removed in a vacuum, the residue is suspended in 100 ml. ethanol and 30 ml. concentrated hydrochloric acid are added thereto, followed by saturation with hydrogen sulphide. The reaction mixture is heated under reflux and the precipitated mercury sulphide is filtered off and then washed with hot ethanol. The filtrate is evaporated to dryness in a vacuum, the residue is dissolved in 100 ml. water, insoluble components are filtered off, the filtrate is rendered alkaline with 2N ammonia solution, the base is filtered off with suction and then washed with water. The product is purified over a silica gel column (elution agent 1,1,1-trichloroethane/methanolic ammonia 15:1 v/v). The appropriate fractions are evaporated in a vacuum, the oil obtained is taken up in hot ethanol, diethyl ether is added thereto until turbidity commences and then left to crystallise. There are obtained 2.8 of the title compound; m.p. 286°–288° C.

EXAMPLE 18

The following compound was obtained in a manner analogous to that described in Example 17:

| designation | yield % | m.p. °C. (solvent) |
|---|---|---|
| (a) 6',7'-dihydro-2'-phenyl-amino-spiro(cyclopentane-1,7'-3'H,5'H—pyrrolo-[2',3'-f]benzimidazol)-6'-one from 5',6'-diamino-spiro[cyclopentane-1,3'-indolin]-2-one and phenyl isothiocyanate | 34 | 290–294 (dichloro-methane) |

EXAMPLE 19

6,7-Dihydro-7,7-dimethyl-2-(3-indolyl)-3H,5H-pyrrolo[2,3-f]benzimidazol-6-one 3.1 g. 5,6-Diamino-3,3-dimethylindolin-2-one and 2.5 g. indole-3-aldehyde are stirred for 4 days at ambient temperature in 150 ml. methanol and 4 ml. glacial acetic acid. The solvent is then removed in a vacuum and the residue is purified by column chromatography on silica gel. The appropriate fractions are combined, the solvent is removed in a vacuum, the residue (3.7 g. of a yellow oil) is dissolved in methanol, dichloromethane added thereto until turbidity commences and then left to crystallise. There are obtained 3.1 g. of the title compound; m.p. 243°–245° C.

EXAMPLE 20

5-Acetyl-7,7-dimethyl-2-(2-methoxy-4-methylsulphonylphenyl)-6,7-dihydro-3H,5H-pyrrolo[2,3-f]benzimidazole (a) A mixture of 6.6 g. (30 mmole) 1-acetyl-5,6-diamino-3,3-dimethylindole, 150 ml. ethanol and 11.4 g. (40 mmole) sodium α-hydroxy-(2-methoxy-4-methylthiophenyl)-methanesulphonate is stirred for 3 hours at ambient temperature while passing in air. The reaction mixture is then mixed with water and aqueous sodium carbonate solution, extracted with dichloromethane, dried and evaporated. After chromatography on silica gel, there are obtained 7.6 g. (66% of theory) 5-acetyl-7,7-dimethyl-2-(2-methoxy-4-methylthiophenyl-6,7-dihydro-3H,5H-pyrrolo[2,3-f]benzimidazole; m.p. 105°–107° C.

(b) 3.8 g. (10 mmole) of the above compound are stirred for 24 hours at ambient temperature in 70 ml. acetic acid and 7 ml. 30% hydrogen peroxide solution. The reaction mixture is mixed with water, evaporated in a vacuum and the residue chromatographed on silica gel. There are obtained 2.3 g. (56% of theory) of the title compound; m.p. 223°–225° C.

EXAMPLE 21

5-Acetyl-7,7-dimethyl-2-phenyl-6,7-dihydro-3H,5H-pyrrolo[2,3-f]benzimidazole

A mixture of 2.2 g. (10 mmole) 1-acetyl-5,6-diamino-3,3-dimethylindoline, 200 ml. methanol, 5.2 ml. acetic acid, 1.0 ml. benzaldehyde and 50 mg. manganese dioxide is stirred for 3 hours at ambient temperature while passing in air. The reaction mixture is then filtered, the filtrate evaporated and the residue chromatographed on silica gel. After evaporation of the appropriate fractions and trituration with diethyl ether, there is obtained 0.8 g. (26% of theory) of the title compound; m.p. 225°–227° C.

EXAMPLE 22

The following compounds were obtained in a manner analogous to that described in Example 21:

| designation | yield % | m.p. °C. (solvent) |
|---|---|---|
| (a) 5-acetyl-7,7-dimethyl-2-n-hexyl-6,7-dihydro-3H,5H—pyrrolo[2,3-f]benzimidazole from 1-acetyl-5,6-diamino-3,3-dimethyl-indoline and heptanal | 35 | 188–190 (dichloro-methane) |
| (b) 5'-acetyl-2'-(4-methoxy-phenyl)-6',7'-dihydro-spiro-(cyclopentane-1,7'-3'H,5'H—pyrrolo[2',3'-f]benzimidazole) from 1'-acetyl-5',6'-diamino-spiro[cyclopentane-1,3'-indoline] and 4-methoxybenzaldehyde | 47 | above 280 (diethyl ether) |
| (c) 5'-acetyl-2'-(4-methoxyphenyl-methyl)-6',7'-dihydrospiro-(cyclopentane-1,7'-3'H,5'H—pyrrolo[2',3'-f]benzimidazole) from 1'-acetyl-5',6'-diamino-spiro[cyclopentane-1,3'-indoline and 4-methoxyphenyl-acetaldehyde | | |
| (d) 5'-acetyl-2'-[2-(4-methoxy-phenyl)-ethenyl]-6',7'-dihydro-spiro(cyclopentane-1,7'-3'H,5'H—pyrrolo[2',3'-f]benzimidazole) from 1'-acetyl-5',6'-diaminospiro-[cyclopentane-1,3'-indoline] and 4-methoxy-cinnamaldehyde | | |
| (e) 7,7-dimethyl-6,7-dihydro-2-(3,4-methylenedioxy-phenyl)-3H,5H—pyrrolo[2,3-f]benzimidazole-6-one from 5,6-diamino-3,3-dimethylindoline and piperonal | 48 | >300 (ethyl acetate) |
| (f) 2'-(3,4-methylenedioxy-phenyl)-6',7'-dihydro-spiro-(cyclopentane-1,7'-3'H,5'H—pyrrolo[2',3'-f]benz-imidazole)-6'-one from 5',6'-diamino-spiro[cyclopentane-1,3'-indolin]-2'-one and piperonal | 45 | >300 (methanol) |
| (g) 2'-(3,4-ethylenedioxyphenyl)-6',7'-dihydro-spiro-(cyclopentane-1,7'-3'H,5'H—pyrrolo-[2',3'-f]benzimidazole)-6'-one from 5',6'-diamino-spiro[cyclopentane-1,3'-indolin]-2'one and 3,4-ethylenedioxybenzaldehyde | 52 | >300 (methanol) |

EXAMPLE 23

The following compounds were obtained in a manner analogous to that described in Example 5:

| designation | yield % | m.p. °C. (solvent) |
|---|---|---|
| (a) 7,7-dimethyl-6,7-dihydro-2-(imidazol-1-yl-methyl)-3H,5H—pyrrolo[2,3-f]benzimidazole dihydrochloride from the | 55 | 181–183 (acetone) |

-continued

| designation | yield % | m.p. °C. (solvent) |
|---|---|---|
| compound of Example 14f | | |
| (b) 7,7-dimethyl-6,7-dihydro-2-(4-pyridylcarbonylamino)-3H,5H—pyrrolo[2,3-f]benzimidazole trihydrochloride from the compound of Example 16g | 46 | 205–207 (acetone) |
| (c) 7,7-dimethyl-2-(2-methoxy-4-methylsulphonyl-phenyl)-6,7-dihydro-3H,5H—pyrrolo[2,3-f]-benzimidazole dihydrochloride from the compound of Example 20 | 71 | 267–268 (ethanol) |
| (d) 7,7-dimethyl-2-n-hexyl-6,7-dihydro-3H,5H—pyrrolo[2,3-f]-benzimidazole dihydrochloride from the compound of Example 22a | 58 | 181–183 (acetone) |
| (e) 2'-(4-methoxyphenyl)-6',7'-dihydro-spiro(cyclopentane-1,7'-3'H,5'H—pyrrolo[2',3'-f]-benzimidazole)dihydrochloride from the compound of Example 22b | 56 | 268–270 (acetone) |
| (f) 2'-(4-methoxyphenylmethyl)-6',7'-dihydro-spiro(cyclopentane-1,7'-3'H,5'H—pyrrolo[2',3'-f]benzimidazole) from the compound of Example 22c | 88 | 95–96 (dichloromethane) |
| (g) 2'-[2-(4-methoxyphenyl)-ethenyl]-6',7'-dihydro-spiro(cyclopentane-1,7'-3'H,5'H—pyrrolo[2',3'-f]benzimidazole) from the compound of Example 22d | 54 | 86–88 (ligroin) |

The pharmaceutical properties of the subject pyrrolobenzimidazole derivatives are shown in the following two examples.

EXAMPLE 24

Investigations of the Hemodynamic Properties

The average arterial pressure, the heart rate and dp/dt$_{max}$ (derivative of the pressure in the left ventricle with respect to time—a measure of the force of the myocardial contraction)—were determined as hemodynamic parameter. Normotensive Sprague Dawley rats were anaesthetized with Inaktin i.p. To Facilitate spontaneous breathing, the animals were provided with a tracheal tube. A Miller Mikro-Tip was placed in the left ventricle to record the left ventricular pressure (LVP) and dp/dt$_{max}$ was determined with the help of a computer. The vena jugularis served as i.v. access. The arterial pressure was measured by means of a catheter and a pressure transducer by way of the arteria femoralis. The EKG and the heart rate were derived by way of subcutaneous puncture electrodes.

For the screening of potential cardiotonics, the doses were fractionated and applied cumulative from 0.01 to 30 mg/kg at 10-minute intervals.

The ED$_{+1.5\ mHg/sec}$ of the substances investigated is given in Table 1. It is understood to be the particular effective dose, which increases the control value by 1.5 mHg/sec. Table 2 shows the behavior of the average arterial pressure and of the heart rate. The starting values (control) were compared with the values after a dose of 1 mg/kg.

TABLE 1

ED$_{+1.5\ mHg/sec}$ = the particular effective dose, which raises the control value by 1.5 mHg/sec.

| Compounds of Example | ED$_{+1.5\ mHg/sec}$ |
|---|---|
| 14 (d) | 0.688 mg/kg |
| 9 | 8.137 mg/kg |
| 14 (c) | 21.22 mg/kg |
| 14 (b) | 2.487 mg/kg |
| 3 | >30.00 mg/kg |
| 12 | 0.2387 mg/kg |

TABLE 2

Average Arterial Blood Pressure : $\bar{p}$
Heart rate: HF $\bar{x} \pm s_x$

| Compound of Example | Control | Dose 1 mg/kg |
|---|---|---|
| 14 (d) | $\bar{p}$: 136 ± 7.3 | 129 ± 8.2 |
| 14 (a) | HF: 353 ± 14.2 | 255 ± 13.4 |
| | 118 | 108 |
| | 315 | 350 |
| 9 | 101 ± 12.8 | 106 ± 9.5 |
| | 263 ± 5.0 | 289 ± 17.0 |
| 14 (c) | 134 ± 5.5 | 125 ± 16.0 |
| | 351 ± 22.5 | 350 ± 17.0 |
| 14 (b) | 134 ± 6.7 | 120 ± 4.4 |
| | 332 ± 5.4 | 358 ± 13.2 |
| 3 | 128 ± 3.5 | 124 ± 12.5 |
| | 367 ± 2.0 | 378 ± 5.0 |
| 12 | 125 ± 8.5 | 110 ± 8.1 |
| | 331 ± 17.0 | 343 ± 15.7 |

EXAMPLE 25

Erythrocyte Aggregation as Parameter of the Hemorheology

The erythrocyte aggregation was determined with the mini-erythrocyte aggregometer of the Myrenne Co., Roetgen, West Germany, [1]. As a measure of the aggregation, this instrument displays a dimensionless index, which increases with the increasing state of aggregation.

The investigations were carried out with human blood from healthy donors. The blood, which was adjusted to a hematocrit of 45%, was incubated with the control solution or with the substance solutions. Subsequently, the erythrocyte aggregation was measured. Each substance was analyzed at a concentration of $10^{-6}$M and $10^{-5}$M. The difference in the aggregation indices between the initial value of the control solution and the values with the substance solution was calculated.

The available findings relating to the erythrocyte aggregation of the above-mentioned substances are lised in Table 3.

On the other hand, at a comparable concentration of $1.7 \times 10^{-5}$M., Venoruton, a mixture of different o-(beta-hydroxyethyl)rutosides, brings about merely a decrease in the erythrocyte aggregation index of 0.38. Even at a concentration of $1.7 \times 10^{-3}$M the reduction in the erythrocyte aggregation is only 3.9±0.9. Venoruton is intended to inhibit the tendency of erythrocytes to aggregate [2]. In comparison with Venoruton, the substances of this invention clearly reduce the erythrocyte aggregation more.

TABLE 3

Erythrocyte Aggregation
in vitro incubation of human blood (hematocrit = 45%)
control: respective solvent
Δ = difference from control value

| Compounds of Example | Control | Δ at $10^{-6}$ M | Δ at $10^{-5}$ M | Δ at $17 \times 10^{-5}$ | n |
|---|---|---|---|---|---|
| 14 (c) | 13.75 | $-0.75 \pm 0.21$ | $-10.5 \pm 1.06$ | | 2 |
| 3 | 13.8 | $-1.6$ | $-6$ | | 1 |
| 9 | 20 | $-2.6 \pm 0.14$ | $-5.65 \pm 3.04$ | | 2 |
| 14 (b) | 11.3 | $-3.3 \pm 0.5$ | $-6.25 \pm 0.7$ | | 2 |
| 14 (a) | 14.1 | $-0.6$ | $-4.7$ | | 1 |
| Venoruton | 12.5 | | | $-0.38 \pm 0.48$ | 6 |

References: [1] Kiesewetter, H., et al., "The mini-erythrocyte aggregometer—a new instrument for the rapid quantification of the extent of erythrocyte aggregation", Biomed. Technik 27 (1982), No. 9, pp. 209–13; [2] Schmid-Schönbein, H., et al., "Effect of o-(beta-hydroxyethyl)-rutosides on the microrheology of human blood under defined flow conditions", VASA 4 (1975), pp. 263–70.

It will be understood that the specification and examples are illustrative but not limitative of the present invention and that other embodiments within the spirit and scope of the invention will suggest themselves to those skilled in the art.

What is claimed is:

1. A pyrrolobenzimidazole compound of the formula

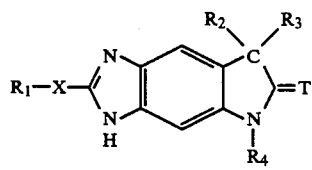

wherein $R_1$ is a phenyl group of the formula

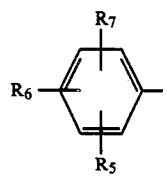

in which $R_5$, $R_6$ and $R_7$, which can be the same or different, each represents: hydrogen, a $C_1$–$C_5$-alkane-sulphonyloxy; trifluoromethanesulphonyloxy; $C_1$–$C_5$-alkane-sulphonylamino; trifluoromethanesulponyl-amino; N-($C_1$–$C_5$-alkyl)-$C_1$–$C_5$-alkanesulphonylamino; N-($C_1$–$C_5$-alkyl)trifluoromethanesulphonylamino; $C_1$–$C_5$-alkyl-sulphenylmethyl, $C_1$–$C_5$-alkylsulphinylmethyl or $C_1$–$C_5$-alkyl-sulphonylmethyl radical; a carbonyl group substituted by hydroxyl, $C_1$–$C_5$-alkoxy, amino, $C_1$–$C_5$-alkylamino or di-($C_1$–$C_5$-alkyl)-amino; a sulphonyl group substituted by amino, $C_1$–$C_5$-alkylamino or di-($C_1$–$C_5$-alkyl)-amino; a $C_1$–$C_5$-alkylcarbonylamino, aminocarbonylamino or $C_1$–$C_5$-alkylamino-carbonylamino radical; a $C_1$–$C_5$-alkylthio, $C_1$–$C_5$-alkylsulphinyl or $C_1$–$C_5$-alkylsulphonyl radical; nitro; halogen; amino; hydroxyl; $C_1$–$C_5$-alkyl; $C_1$–$C_5$-alkoxy; $C_2$–$C_5$-alkenyloxy; $C_2$–$C_5$-alkynyloxy; cyano-($C_1$–$C_5$-alkyl)-oxy; carboxy-($C_1$–$C_5$-alkyl)-oxy; $C_1$–$C_5$-alkoxy-carbonyl-($C_1$–$C_5$-alkyl)-oxy; di-($C_1$–$C_5$-alkyl)-amino; 1-imidazolyl; trifluoromethyl or cyano;

or $R^1$ is a naphthyl radical;

a heterocyclic radical selected from the group consisting of furan, pyrrole, thiophene, benzimidazole, indole, benzofuran, benzothiophene, pyrazole and imidazole, all of which may be optionally substituted one or more times by $C_1$–$C_6$-alkyl, $C_1$–$C_6$-alkoxy, $C_1$–$C_6$-alkylthio, hydroxyl, nitro, amino, halogen or cyano; or when X represents a valency bond, $R_1$ can additionally also represent hydrogen, $C_1$–$C_{10}$-alkyl, $C_3$–$C_7$-cycloalkyl, $C_2$–$C_{10}$-alkenyl, $C_4$–$C_7$-cycloalkenyl, $C_2$–$C_{10}$-alkynyl, $C_1$–$C_{10}$-haloalkyl, $C_2$–$C_{20}$-alkoxyalkyl, carboxyl-$C_1$–$C_{10}$-alkyl, $C_1$–$C_{10}$-alkoxycarbonyl-$C_1$–$C_{10}$-alkyl, $C_1$–$C_{10}$-aminoalkyl, $C_1$–$C_{10}$-hydroxyalkyl, hydroxyl, mercapto, amino, $C_1$–$C_{10}$-alkylthio, $C_1$–$C_{10}$-alkylcarbonylamino, formylamino, $C_1$–$C_{10}$-alkylsulphonylamino, formylamino-$C_1$–$C_{10}$-alkyl, $C_1$–$C_{10}$-alkoxycarbonyl-$C_1$–$C_{10}$-aminoalkyl or $C_1$–$C_{10}$-alkylsulphonylamino-$C_1$–$C_{10}$-alkyl;

$R_2$ is hydrogen, $C_1$–$C_6$-alkyl, $C_2$–$C_6$-alkenyl or $C_3$–$C_7$-cycloalkyl;

$R_3$ is $C_1$–$C_6$-alkyl, $C_2$–$C_6$-alkenyl or $C_1$–$C_6$-hydroxyalkyl;

or $R_2$ and $R_3$ together with the carbon atom to which they are attached represent a $C_3$–$C_7$-cycloalkyl group; or together form a $C_3$–$C_6$ alkylidene or $C_4$–$C_7$-cycloalkylidene radical;

$R_4$ is hydrogen or $C_1$–$C_7$-alkanoyl;

X is a valency bond, a $C_1$–$C_4$-alkylene or vinylene radical, an imino group (—NH—) or a carbonylamino group (—CONH—);

T stands for two hydrogen atoms or, when X is an imino group (—NH—) or a carbonylamino group (—CONH—) or, when $R_1$ is a bicyclic radical, also an oxygen atom;

the tautomers thereof and the physiologically acceptable salts thereof with inorganic and organic acids.

2. A pyrrolobenzimidazole compound according to claim 1 in which each of $R_2$ and $R_3$ is a methyl, ethyl, propyl or butyl radical, or $R_2$ and $R_3$, together with the carbon atom to which they are attached, represent $C_3$–$C_6$-cycloalkyl $R_4$ is hydrogen or $C_1$–$C_3$ alkanoyl, and X is a valency bond, methylene, ethylene, an imino group or a carbonylamino group.

3. A pyrrolobenzimidazole compound according to claim 2 in which $R_1$ is a phenyl group wherein $R_5$ is: hydrogen; a $C_1-C_2$-alkylsulphonyloxy, trifluoromethylsulphonyloxy, $C_1-C_2$-alkylsulphenylmethyl, $C_1-C_2$-alkylsulphinylmethyl, $C_1-C_2$-alkylsulphonylmethyl, $C_1-C_2$-alkylsulphonylamino, N-($C_1-C_2$-alkyl)-$C_1-C_2$-alkylsulphonylamino, trifluoromethylsulphonylamino or N-($C_1-C_2$-alkyl)-trifluoromethylsulphonylamino radical; a carbonyl group substituted by hydroxyl, $C_1-C_2$-alkoxy, amino, $C_1-C_2$-alkylamino or di-($C_1-C_2$-alkyl)-amino; a sulphonyl group substituted by amino or di-($C_1-C_2$-alkyl)-amino; nitro; cyano; $C_1-C_4$-alkylaminosulphonyl; $C_1-C_2$-alkylcarbonylamino; aminocarbonylamino or N-($C_1-C_2$-alkyl)-aminocarbonylamino; $C_1-C_2$-alkylthio; $C_1-C_2$-alkylsulphinyl; $C_1-C_2$-alkylsulphonyl; halogen; amino; hydroxyl; di-($C_1-C_3$-alkyl)-amino; $C_1-C_3$-alkyl; $C_1-C_3$-alkoxy; $C_2-C_3$-alkenyloxy; $C_2-C_3$-alkynyloxy; cyanomethyloxy; methoxycarbonylmethyloxy; trifluoromethyl; or 1-imidazolyl radical;

$R_6$ is hydrogen; $C_1-C_3$-alkyl, $C_1-C_2$-alkoxy or di-($C_1-C_2$-alkyl)-amino; or halogen; and $R_7$ is hydrogen or methoxy.

4. A pyrrolobenzimidazole compound according to claim 2 in which $R_1$ is a phenyl group wherein $R_5$ is hydroxy, $C_1-C_3$-alkyl, $C_1-C_3$-alkoxy, allyloxy, propargyloxy, cyanomethyloxy, methoxycarbonylmethyloxy, halogen, nitro, cyano, aminocarbonyl, methoxycarbonyl, amino, $C_1-C_3$-dialkylamino, $C_1-C_3$-alkylthio, $C_1-C_3$-alkylsulphonyl, $C_1-C_3$-alkylsulphonyloxy or 1-imidazolyl; and each of $R_6$ and $R_7$ is hydrogen.

5. A pyrrolobenzimidazole compound according to claim 2 in which $R_1$ is a phenyl group wherein each of $R_5$ and $R_6$, which may be the same or different, is: a $C_1-C_3$-alkanesulphonyloxy, trifluoromethylsulphonyloxy, $C_1-C_3$-alkylsulphenylmethyl, $C_1-C_3$-alkylsulphinylmethyl, $C_1-C_3$-alkylsulphonylmethyl, $C_1-C_3$-alkylsulphonylamino, N-($C_1-C_3$-alkyl)-$C_1-C_3$-alkylsulphonylamino, trifluoromethylsulphonylamino or N-($C_1-C_3$-alkyl)-trifluoromethylsulphonylamino radical; a carbonyl group substituted by hydroxyl, $C_1-C_3$-alkoxy, amino, $C_1-C_3$-alkylamino or di-($C_1-C_3$-alkyl)-amino; a sulphonyl group substituted by amino or di-($C_1-C_3$-alkyl)-amino; $C_1-C_3$-alkylaminosulphonyl; $C_1-C_3$-alkylcarbonylamino; aminocarbonylamino; N-($C_1-C_3$-alkyl)-aminocarbonylamino; hydroxyl; $C_1-C_3$-alkyl; $C_1-C_3$-alkoxy; allyloxy, propargyloxy; cyanomethyloxy; methoxycarbonylmethyloxy; cyano; halogen; nitro; amino; di-($C_1-C_3$-alkyl)-amino; $C_1-C_3$-alkylthio; $C_1-C_3$-alkylsulphinyl, $C_1-C_3$-alkylsulphonyl; or 1-imidazolyl; and $R_7$ is hydrogen.

6. A pyrrolobenzimidazole compound according to claim 5 in which the substitutents $R_5$ and $R_6$ are in 2,4-, 2,5- or 3,4-positions.

7. A pyrrolobenzimidazole compound according to claim 3 in which $R_1$ is 3,4,5-trimethoxyphenyl.

8. A pyrrolobenzimidazole compound according to claim 2 in which $R_1$ is pyrrole, furan, thiophene, pyrazole, or imidazole, optionally substituted by methyl, ethyl, methoxy, ethoxy, methylthio or ethylthio.

9. A pyrrolobenzimidazole compound according to claim 2 in which $R_1$ is indole, benzimidazole, benzofuran, benzothiophene or naphthyl.

10. A pyrrolobenzimidazole compound according to claim 2 in which X is a valency bond, and $R_1$ is methyl, ethyl, propyl, butyl, pentyl, hexyl, vinyl, propenyl, propynyl, cyclopropyl, cyclobutyl, cyclopentyl, cyclohexyl, cyclopentenyl, cyclohexenyl, trifluoromethyl, ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, aminomethyl, aminoethyl, aminopropyl, aminobutyl, hydroxymethyl, hydroxyethyl, hydroxypropyl, hydroxybutyl, methylthio, ethylthio, propylthio, butylthio, acetylamino, propionylamino, butyloxycarbonylamino, methylsulphonylamino, formylaminopropyl, acetylaminopropyl, propionylaminopropyl and methylsulphonylaminopropyl.

11. A pyrrolobenzimidazole compound according to claim 1, wherein $R_1$ is a phenyl group in which: $R_5$ is hydrogen, methanesulphonyloxy, trifluoromethanesulphonyloxy, methanesulphonylamino, trifluoromethanesulphonylamino, methylthio, methylsulphinyl, methylsulphonyl, hydroxyl, methyl, methoxy, propargyloxy, trifluoromethyl or 1-imidazolyl; $R_6$ is hydrogen, chlorine, methyl, methoxy or dimethylamino; and $R_7$ is hydrogen or methoxy; pyrrole, furan, thiophene, pyrazole or imidazole or the methyl-, ethyl-, methoxy-, ethoxy-, methylthio-, ethylthio- or chlorine-substituted derivatives thereof;

indole or naphthyl; or when X is a valency bond, $R_1$ can additionally represent hydrogen, methyl, ethyl, propyl, butyl, pentyl, hexyl, propenyl, cyclopentyl, cyclohexyl, trifluoromethyl, hydroxyl, mercapto, methylthio, amino, acetamido or formamide;

$R_2$ and $R_3$ are both methyl;

or $R_2$ and $R_3$, together with the carbon atom to which they are attached, form a cyclopentane or cyclohexane ring;

$R_4$ is hydrogen, formyl, acetyl, propionyl or butyryl; and

X is a valency bond, methylene, an imino group or a carbonyl amino group.

12. The compound according to claim 11 which is 7,7-dimethyl-6,7-dihydro-2-phenyl-3H,5H-pyrrolo-[2,3-f]benzimidazole dihydrochloride.

13. The compound according to claim 11 which is 7,7-dimethyl-2-(2-indolyl)-6,7-dihydro-3H,5H-pyrrolo-[2,3-f]benzimidazol-6-one.

14. A pharmaceutical composition comprising an effective amount of a pyrrolobenzimidazole compound according to claim 1 and a pharmaceutically acceptable carrier.

15. A method for the treatment of heart and circulatory diseses which comprises administering an effective amount of a compound of the formula

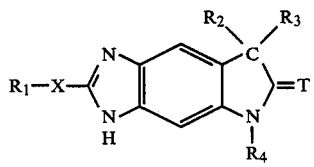

wherein
R₁ is
a phenyl group of the formula

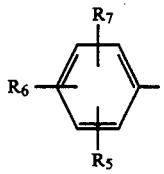

in which
R₅, R₆ and R₇, which can be the same or different, each represents: hydrogen; a $C_1$-$C_5$-alkanesulphonyloxy, trifluoromethanesulphonyloxy; $C_1$-$C_5$-alkane-sulphonylamino; trifluoromethanesulphonyl-amino; N-$C_1$-$C_5$-alkyl-$C_1$-$C_5$-alkanesulphonylamino; N-$C_1$-$C_5$-alkyltrifluoromethanesulphonylamino; $C_1$-$C_5$-alkyl-sulphenylmethyl; $C_1$-$C_5$-alkylsulphinylmethyl or $C_1$-$C_5$-alkyl-sulphonylmethyl radical; a carbonyl group substituted by hydroxyl, $C_1$-$C_5$-alkoxy, amino, $C_1$-$C_5$-alkylamino or di-($C_1$-$C_5$-alkyl)-amino; a sulphonyl group substituted by amino, $C_1$-$C_5$-alkylamino or di-($C_1$-$C_5$-alkyl)-amino; a $C_1$-$C_5$-alkylcarbonylamino, aminocarbonylamino or $C_1$-$C_5$-alkylaminocarbonylamino radical; a $C_1$-$C_5$-alkylthio, $C_1$-$C_5$-alkylsulphinyl or $C_1$-$C_5$-alkylsulphonyl radical; nitro; halogen; amino; hydroxyl; $C_1$-$C_5$-alkyl; $C_1$-$C_5$-alkoxy; $C_2$-$C_5$-alkenyloxy; $C_2$-$C_5$-alkynyloxy; cyano-($C_1$-$C_5$-alkyl)-; carboxy-($C_1$-$C_5$-alkyl)-; $C_1$-$C_5$-alkoxycarbonyl-($C_1$-$C_5$-alkyl)-; di-($C_1$-$C_5$-alkyl)-amino; 1-imidazolyl; trifluoromethyl or cyano;
or R₁ is a naphthyl radical;
a heterocyclic radical selected from the group consisting of furan, pyrrole, thiophene, benzimidazole, indole, benzofuran, benzothiophene, pyrazole and imidazole, all of which may be optionally substituted one or more times by $C_1$-$C_6$-alkyl, $C_1$-$C_6$-alkoxy, $C_1$-$C_6$-alkylthio, hydroxyl, nitro, amino, halogen or cyano; or
when X represents a valency bond, R₁ can additionally also represent hydrogen, $C_1$-$C_{10}$-alkyl, $C_3$-$C_2$-cycloalkyl, $C_2$-$C_{10}$-alkenyl, $C_4$-$C_7$-cycloalkenyl, $C_2$-$C_{10}$-alkynyl, $C_1$-$C_{10}$-haloalkyl, $C_2$-$C_{20}$akoxyalkyl, carboxyl-$C_1$-$C_{10}$-alkyl, $C_1$-$C_{10}$-alkoxycarbonyl-$C_1$-$C_{10}$-alkyl, $C_1$-$C_{10}$-aminoalkyl, $C_1$-$C_{10}$-hydroxyalkyl, hydroxyl, mercapto, amino, $C_1$-$C_{10}$-alkylthio, $C_1$-$C_{10}$-alyl-carbonylamino, formylamino, $C_1$-$C_{10}$-alkylsulphonylamino, formylamino-$C_1$-$C_{10}$-alkyl, $C_1$-$C_{10}$-alkoxycarbonyl-$C_1$-$C_{10}$-aminoalkyl or $C_1$-$C_{10}$-alkylsulphonylamino-$C_1$-$C_{10}$-alkyl;
R₂ is hydrogen, $C_1$-$C_6$-alkyl, $C_2$-$C_6$-alkenyl or $C_3$-$C_7$-cycloalkyl;
R₃ is $C_1$-$C_6$-alkyl, $C_2$-$C_6$-alkenyl or $C_1$-$C_6$-alkenyl or $C_1$-$C_6$-hydroxyalkyl;
or R₂ and R₃ together with the carbon atom to which they are attached represent a $C_3$-$C_7$-cycloalkyl group; or together form a $C_3$-$C_6$ alkylidene or $C_4$-$C_7$-cycloalkylidene radical;
R₄ is hydrogen or $C_1$-$C_7$-alkanoyl;
X is a valency bond, a $C_1$-$C_4$-alkylene or vinylene radical, an imino group (—NH—) or a carbonylamino group (—CONH—);
T stands for two hydrogen atoms or, when X is an imino group (—NH—) or a carbonylamino group (—CONH—) or when R₁ is a bicyclic radical, also an oxygen atom;
the tautomers thereof and the physiologically acceptable salts thereof with inorganic and organic acids.

16. A method according to claim 15 wherein, in the compound,
R₁ is
a phenyl group in which: R₅ is hydrogen, methanesulphonyloxy, trifluoromethanesulphonyloxy, methanesulphonylamino, trifluoromethanesulphonylamino, methylthio, methylsulphinyl, methylsulphonyl, hydroxyl, methyl, methoxy, propargyloxy, trifluoromethyl or 1-imidazolyl; R₆ is hydrogen, chlorine, methyl, methoxy or dimethylamino; and R₇ is hydrogen or methoxy;
pyrrole, furan, thiophene, pyrazole or imidazole or the methyl-, ethyl-, methoxy-, ethoxy-, methylthio-, ethylthio- or chlorine-substituted derivatives thereof;
indole or naphthyl; or
when X is a valency bond, R₁ can additionally represent hydrogen, methyl, ethyl, propyl, butyl, pentyl, hexyl, propenyl, cyclopentyl, cyclohexyl, trifluoromethyl, hydroxyl, mercapto, methylthio, amino, acetamido or formamide;
R₂ and R₃ are both methyl;
or R₂ and R₃, together with the carbon atom to which they are attached, form a cyclopentane or cyclohexane ring;
R₄ is hydrogen, formyl, acetyl, propionyl or butyryl; and
X is a valency bond, methylene, an imino group or a carbonyl amino group.

17. A method according to claim 15 wherein from about 5 to about 500 mg of compound are administered per 75 Kg of body weight per day.

18. A method according to claim 15, which comprises the treatment of peripheral arterial occlusive diseases as well as venous insuffiency.

19. A composition according to claim 14 in which the compound is
7,7-dimethyl-6,7-dihydro-2-phenyl-3H,5H-pyrrolo-[2,3-f]benzimidazole dihydrochloride or
7,7-dimethyl-2-(2-indolyl)-6,7-dihydro-3H,5H-pyrrolo-[2,3-f]benzimidazol-6-one.

20. A method according to claim 16, in which the compound is
7,7-dimethyl-6,7-dihydro-2-phenyl-3H,5H-pyrrolo-[2,3-f]benzimidazole dihydrochloride or
7,7-dimethyl-2-(2-indolyl)-6,7-dihydro-3H,5H-pyrrolo[2,3-f]benzimidazol-6-one.

* * * * *